United States Patent
Cavani et al.

(10) Patent No.: US 11,932,592 B2
(45) Date of Patent: Mar. 19, 2024

(54) PROCESS FOR THE TRANSFORMATION OF PRIMARY ALIPHATIC ALCOHOLS INTO HIGHER ALIPHATIC ALCOHOLS

(71) Applicant: ALMA MATER STUDIORUM—UNIVERSITA' DI BOLOGNA, Bologna (IT)

(72) Inventors: Fabrizio Cavani, Modena (IT); Valerio Zanotti, Bologna (IT); Rita Mazzoni, Casalecchio di Reno (IT); Carlo Lucarelli, Bologna (IT); Cristiana Cesari, Ascoli Piceno (IT); Tommaso Tabanelli, Cotignola (IT); Francesco Puzzo, Pietraperzia (IT)

(73) Assignee: ALMA MATER STUDIORUM—UNIVERSITA' DI BOLOGNA, Bologna (IT)

( * ) Notice: Subject to any disclaimer, the term of this patent is extended or adjusted under 35 U.S.C. 154(b) by 786 days.

(21) Appl. No.: 17/044,906

(22) PCT Filed: Apr. 4, 2019

(86) PCT No.: PCT/EP2019/058459
§ 371 (c)(1),
(2) Date: Oct. 2, 2020

(87) PCT Pub. No.: WO2019/193079
PCT Pub. Date: Oct. 10, 2019

(65) Prior Publication Data
US 2021/0163385 A1    Jun. 3, 2021

(30) Foreign Application Priority Data
Apr. 5, 2018 (IT) .................. 102018000004226

(51) Int. Cl.
*C07C 29/34* (2006.01)
*B01J 31/20* (2006.01)
*B01J 31/22* (2006.01)
*C07C 29/94* (2006.01)

(52) U.S. Cl.
CPC .............. *C07C 29/34* (2013.01); *B01J 31/20* (2013.01); *B01J 31/2295* (2013.01); *C07C 29/94* (2013.01); *B01J 2231/44* (2013.01); *B01J 2531/821* (2013.01)

(58) Field of Classification Search
CPC ..................................... C07C 29/34
See application file for complete search history.

(56) References Cited

U.S. PATENT DOCUMENTS

| 9,266,807 | B1 | 2/2016 | Norman et al. |
| 2010/0298613 | A1 | 11/2010 | Tanaka et al. |
| 2013/0116481 | A1 | 5/2013 | Wass et al. |

FOREIGN PATENT DOCUMENTS

| JP | 2007223947 A | 9/2007 |
| JP | 2008266267 A | 11/2008 |
| JP | 2008303160 A | 12/2008 |
| JP | 2011136970 A | 7/2011 |
| JP | 2011225454 A | 11/2011 |
| WO | 2015031561 A1 | 3/2015 |

OTHER PUBLICATIONS

Mazzoni, R. et al. "Catalytic Biorefining of Ethanol from Wine Waste to Butanol and Higher Alcohols: Modeling the Life Cycle Assessment and Process Design" ACS Sustainable Chem. Eng. 2019, 7, 224-237; published Nov. 20, 2018 (Year: 2018).*
International Search Report and Written Opinion for Corresponding International Application No. PCT/EP2019/058459 (9 Pages) (dated Jun. 18, 2019).

* cited by examiner

*Primary Examiner* — Medhanit W Bahta
(74) *Attorney, Agent, or Firm* — Lucas & Mercanti, LLP

(57) ABSTRACT

A process for obtaining higher aliphatic alcohols starting from aliphatic primary alcohols by condensation reactions is disclosed. Specifically, the process comprises a step in which an aliphatic primary alcohol is contacted in a homogeneous phase with a catalyst mixture comprising a transition metal, a base and an additive; specifically, this additive can be selected from the classes of compounds of the isoquinolines N-oxide, quinolines N-oxide, pyridines N-oxide, benzoquinones, naphthoquinones, or TEMPO. In particular, the process can be carried out by contacting said aliphatic primary alcohol with a catalyst of a recycled transition metal, with a freshly added base and with a recycled additive of the aforementioned type.

20 Claims, No Drawings

PROCESS FOR THE TRANSFORMATION OF PRIMARY ALIPHATIC ALCOHOLS INTO HIGHER ALIPHATIC ALCOHOLS

CROSS-REFERENCE TO RELATED APPLICATIONS

This application is a 371 of PCT/EP2019/058459, filed Apr. 4, 2019, which claims the benefit of Italian Patent Application No. 102018000004226, filed Apr. 5, 2018.

FIELD OF APPLICATION

The present invention relates to a process belonging to the field of organic synthesis in homogeneous catalysis.

Specifically, the present invention relates to a process for obtaining higher aliphatic alcohols starting from primary aliphatic alcohols.

BACKGROUND ART

The applications of ethanol as a basic chemical material rise increasing interest due to environmental reasons in relation to the ever-increasing development of new processes for refining and processing vegetable biomasses, as opposed to traditional petrochemical processes.

In fact, the so-called "bio-ethanol" has been shown to be an ecologically sustainable basic chemical reagent as well as a biofuel, respectively valid as a substitute for reagents deriving from the refining of crude oil or fossil fuels, in particular when derived from herbaceous plants or derivatives thereof not intended for food supply (C. Angelici et al., ChemSusChem 2013, 6, 1595-1614).

The catalytic conversion of ethanol into butanol and higher alcohols is a promising pathway for the transformation of an easily obtainable and low-cost substance into molecules with greater added value for the industry, for example, into butanol or C4 and higher aliphatic alcohols mixtures, which have chemical-physical properties similar to those of gasoline.

In this context, the Guerbet's reaction, known for over a century, provides an ideal mechanism for this type of transformation. See Scheme 1 below.

Scheme 1

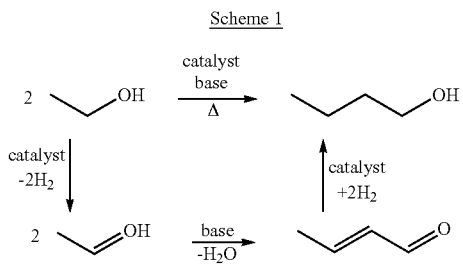

Despite the apparent simplicity of the mechanism, this reaction shows different complications in obtaining high yields and good selectivity; this is also due to the tendency of butanol to undergo consecutive reactions leading to the formation of alcohols having a greater molecular weight, which are often completely undesired secondary products. In particular, the base-catalyzed aldolic condensation of acetaldehyde is particularly difficult to control and is known to lead to the formation of still well exploitable mixtures of higher alcohols (with C6 and/or C8 aliphatic chains) and polymeric material which instead drastically reduces the selectivity and the yield in high added value higher primary aliphatic alcohols (R. J. Davis et al., ACS Catal.; 2013, 3, 1588-1600).

Therefore, recently, trying to improve this reaction from the point of view of the yield of valuable higher aliphatic alcohols and of the selectivity towards n-butanol, the research has focused its efforts to the optimization of homogeneous catalytic systems.

For example, catalytic systems of the homogeneous type based on transition metals such as iridium, rhodium and ruthenium have been developed with the aim of improving the yields and the selectivity towards n-butanol, varying the ligands to these metals (D. Wass et al., ACS Catal. 2016, 6, 7125-7132).

However, in the light of very recent studies, it would seem possible to obtain high selectivity towards n-butanol only by significantly lowering the yield thereof, working at low ethanol conversions.

Among the first examples Tanaka Y. and Utsunomiya M. patented a ruthenium based homogeneous catalytic system active in the Guerbet reaction (US20100298613).

Then, in a study by Wass et al., using ruthenium-based catalysts with phosphine ligands, it was possible to obtain a maximum selectivity of 93% with a yield of 20%. At the same time, in an attempt to increase this obviously not satisfactory yield, similar experiments have led to obtain a 45.8% yield, but causing a lowering of selectivity to 84% (D. Wass et al., Angew. Chem. Int., 2013, 52, 9005-9008).

The same group reported about the use of fermentation broths in order to show some water tolerance of their ruthenium catalysts (D. Wass et al. Catal. Sci. Technol. 2017, 7, 5128-5134, WO201531561).

Similar results were obtained by K. Szymczak et al., using ruthenium-based catalysts with ligands bearing a donor nitrogen (K. Szymczak et al., Chem. Commun., 2016, 52, 2901-2904).

To date, the best results for this type of reaction in terms of selectivity towards butanol have been obtained by Baker and Jones et al. using a tandem catalytic approach, exploiting iridium complexes combined with inorganic bases (10% by moles) or copper complexes (10% by moles) or nickel complexes (10% by moles). The latter cases allow to avoid the use of the aforementioned inorganic bases, where these have been always used according to the approaches listed above. Following this last procedure, i.e. in the absence of inorganic bases, the Guerbet's reaction leads to the formation of n-butanol with a yield of 37% and with a selectivity of 99% (T. Baker, W. D. Jones et al., J. Am. Chem. Soc., 2015, 137, 14264-14267).

The most promising results regarding the use of homogeneous catalysis for the transformation of primary aliphatic alcohols into valuable higher aliphatic alcohols (with particular reference to C4, C6 and C8 aliphatic chains) have been reported even more recently by the group of D. Milstein et al. (D. Milstein et al. J. Am. Chem. Soc. 2016, 138, 9077-9080) who, using a ruthenium catalyst bearing a tridentate ligand and an inorganic base (NaOEt, 20% by moles), obtains a conversion of ethanol of 73.4% towards the formation of n-butanol (yield 35.8%) and valuable higher alcohols: n-hexanol (yield 28.2%) and n-octanol (yield 9.4%) with a reaction temperature of 150° C. and a reaction time (referred to the aforementioned best data) of 40 hours.

Therefore, although obtaining a satisfactory selectivity towards n-butanol maintaining high conversion levels (73.4%), the processes developed by Milstein et al. provide very long reaction times.

Moreover, recently, Jones et al. have shown that even manganese-based complexes with tridentate ligands can be used in the condensation reaction of ethanol to mixtures of higher alcohols in homogeneous catalysis (W. D. Jones et al. ACS Catal., 2018, 8, 997-1002).

Therefore, it is particularly felt the need to improve the catalytic conditions of the Guerbet's reaction for the controlled condensation of primary aliphatic alcohols, in particular for the condensation of ethanol to obtain n-butanol or valuable higher alcohols allowing to obtain high yields in butanol and mixture of alcohols of interest, maintaining high selectivity towards these products, suppressing the polymerization reactions leading to the formation of high molecular weight immiscible macromolecules.

The technical problem underlying the present invention is therefore providing a process for the controlled condensation of primary aliphatic alcohols which enables the aforementioned problems to be overcome and thus guarantees at the same time high yields with respect to the alcohols of interest, guaranteeing at the same time a high selectivity towards shorter chain alcohols (e.g. butanol).

SUMMARY OF THE INVENTION

This technical problem is solved, according to the present invention, by a condensation method in a homogeneous phase of a primary aliphatic alcohol comprising a step in which this primary aliphatic alcohol is contacted with a catalyst mixture, wherein such catalyst mixture comprises:
- a) a catalyst comprising a complex of a transition metal of groups 7-11, wherein said transition metal is selected from the group consisting of Mn, Re, Fe, Ru, Os, Co, Rh, Ir, Ni, Pd, Pt and Cu;
- b) a base;
- c) an additive, wherein said additive is selected from any one of the classes of compounds of the group consisting of pyridines N-oxide, isoquinolines N-oxide, quinolines N-oxide, benzoquinones, naphthoquinones, TEMPO and derivatives thereof.

According to the present invention, the term "base" means a base according to the Brønsted-Lowry acid-base theory.

Advantageously, the process according to the present invention allows to carry out the condensation reaction of a primary aliphatic alcohol towards a mixture of higher aliphatic alcohols, usable in a mixture or easily separable through distillation operations, guaranteeing a high yield in the mixture towards valuable alcohols and maintaining a selective preference towards a dimer of such primary aliphatic alcohol. By just adding an additive of the aforementioned type to the reaction environment, a substantial increase in the conversion and simultaneous yield in the linear dimer as a main product and in the valuable higher alcohols is also obtained.

Moreover, as will be seen later with reference to the detailed description, the use of the aforementioned additive guarantees a reaction pathway such that it is possible to obtain a high conversion of the aforementioned primary aliphatic alcohol and a simultaneous yield in the dimer thereof as a main product, as well as in such higher alcohols, at reaction times that are clearly shorter than those in the background art.

In fact, the present invention allows to carry out the aforementioned transformation from primary aliphatic alcohol to higher aliphatic alcohols with a rate 4 to 10 times higher if the used additive is of the benzoquinone family, and up to 120 times higher if the reaction is carried out using an additive of the isoquinolines N-oxide family with a significant impact on costs and process management. The higher yield towards the dimer of such primary aliphatic alcohol guarantees at the same time selectivity comparable or higher with respect to the known transformations carried out in the sole presence of a catalyst comprising a complex of a transition metal of groups 7-11 and a base, carrying out this transformation in the presence of the same catalyst comprising a complex of a transition metal of groups 7-11 and of the same base, but with the addition of an additive of the aforesaid type.

Advantageously, the aforementioned catalysts and additives can be recovered and re-used, after removing the products and adding a fresh base amount, while maintaining the same efficiency in terms of yield in higher alcohols and selectivity with a significant impact on the costs of the process.

In particular, the present invention allows, through the use of compounds belonging to the aforementioned classes of additives, to increase the yield in higher alcohols with respect to the same complex in the absence of additive and allows to speed up the reaction with respect to the background art while maintaining a high yield towards the dimer of such primary aliphatic alcohol.

The reaction does not require further solvents in addition to the aforementioned primary aliphatic alcohol acting both as reagent and solvent.

According to a preferred embodiment of the present invention, the aforementioned additive belongs to the class of pyridines N-oxide or derivatives thereof.

More preferably, when it belongs to the class of pyridines N-oxide or derivatives thereof, this additive can be a pyridine N-oxide substituted in position 2 and/or 3 and/or 4 with one or more substituents individually and independently selected from any one of the elements of the group consisting of an aliphatic alkyl group, an aromatic group, halogen, hydroxyl, alkoxy and a nitro group. More generally, this substituent at position 2 and/or 3 and/or 4 can be an electron-donor group or an electron-attractor group.

Preferably, this additive belongs to the class of isoquinolines N-oxide or quinolines N-oxide or derivatives thereof.

More preferably, when it belongs to the class of isoquinolines N-oxide or quinolines N-oxide or derivatives thereof, this additive can be an isoquinoline N-oxide or quinoline N-oxide substituted in position 6 and/or 8 with one or more substituents individually and independently selected from any one of the elements of the group consisting of an aliphatic alkyl group, an aromatic group, halogen, hydroxyl, alkoxy and a nitro group. More generally, this substituent at position 6 and/or 8 can be an electron-donor group or an electron-attractor group.

In an equally preferred manner, this additive is isoquinoline N-oxide.

Preferably, this additive belongs to the class of benzoquinones or derivatives thereof.

More preferably, when it belongs to the class of benzoquinones, or derivatives thereof, this additive can belong to the class of p-benzoquinones.

When this additive belongs to the class of p-benzoquinones, this additive can be a 2,6-disubstituted p-benzoquinone, wherein this 2,6-disubstituted p-benzoquinone is substituted with substituents individually and independently selected from any one of the elements of the group consisting of C2-C4 alkyl, C2-C4 alkoxy, hydroxyl, amino, and —NHCOR, wherein R=C2-C4 alkyl.

Even more preferably, when it belongs to the class of p-benzoquinones, this additive can be 2,6-dialkyl-1,4-benzoquinone, even more preferably 2,6-dimethoxy-1,4-benzoquinone.

In an equally preferred manner, when it belongs to the class of p-benzoquinones, this additive can be p-benzoquinone (1,4-benzoquinone).

Preferably, this additive belongs to the class of naphthoquinones or derivatives thereof.

More preferably, when it belongs to the class of naphthoquinones, or derivatives thereof, this additive can be a naphthoquinone substituted in position 2 and/or in position 3 with one or more substituents individually and independently selected from any one of the elements of the group consisting of an aliphatic alkyl group, hydroxyl, alkoxy and halogen.

More generally, this substituent at position 2 and/or 3 can be an electron-donor group or an electron-attractor group.

Preferably, this additive belongs to the class of TEMPO (2,2,6,6-tetramethylpiperidine-1-oxyl), or derivatives thereof.

More preferably, when it belongs to the class of TEMPO (2,2,6,6-tetramethylpiperidine-1-oxyl), or derivatives thereof, this additive can be substituted in position 4 by a substituent selected from any one of the elements of the group consisting of oxo (=O, i.e. oxygen bound by double covalent bond to the six-atoms ring carbon), hydroxyl, alkoxy, amino group, amide group, carboxyl group, and ester group.

In an equally preferred manner, this additive can be 2,2,6,6-tetramethylpiperidine-1-oxyl (TEMPO).

Preferably, the present invention relates to a condensation process of a primary aliphatic alcohol comprising a step of the aforementioned type wherein said primary aliphatic alcohol is a C2-C8 alcohol or any mixture thereof, more preferably said primary aliphatic alcohol is a C2-C4 alcohol.

Even more preferably, said primary aliphatic alcohol is ethanol.

Preferably, the present invention comprises a step of the aforesaid type wherein the aforementioned catalyst comprising a complex of a transition metal of groups 7-11 can comprise a ligand selected from any one of the ligand classes of the group consisting of imidazolium salts, cyclopentadienones, cyclopentadienyls, carbonyl ligands, anionic ligands, ligands comprising at least one electron donor nitrogen, phosphine ligands, water, cyclooctadiene, aryls, and a combination thereof.

More preferably, the aforementioned anionic ligands can be halides, pseudo-halides or hydroxyl.

More preferably, the aforementioned ligand is a ligand comprising at least one donor nitrogen, more preferably said ligand being an amine or a pyridine.

Even more preferably, when it is an amine or a pyridine, this ligand is multi-dentate, i.e. a bidentate ligand, a tridentate ligand, or a tetradentate ligand.

In an equally preferred manner, the aforementioned ligand is a phosphine, more preferably an alkyl phosphine or aryl phosphine, even more preferably this ligand is a multidentate phosphine, i.e. a bidentate phosphine, a tridentate phosphine or a tetradentate phosphine.

Most preferably, the aforementioned ligand is an imidazolium salt (acting as a counterion) having the following general formula I

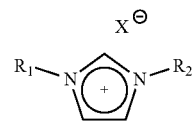

wherein R1 and R2 are substituents independently selected from the elements of the group consisting of hydrogen, C1-C5 alkyl and aryl, preferably said C1-C5 alkyl is methyl, ethyl, n-propyl, iso-propyl, n-butyl, iso-butyl or tert-butyl; and wherein X is chlorine, bromine or iodine.

Preferably, when it is an imidazolium salt having the above formula I, this ligand is 1,3-dimethylimidazolium chloride, 1,3-dimethylimidazolium bromide or 1,3-dimethylimidazolium iodide.

Consistently, the present invention relates to a condensation process of a primary aliphatic alcohol comprising a step of the aforementioned type wherein this catalyst comprising a complex of a transition metal of groups 7-11 is a complex having the following general formula II

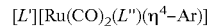

wherein L' is a cation of the imidazolium or any one of substituted derivatives thereof, wherein L" is halogen, and wherein Ar is an aryl, preferably wherein L' is 1,3-dimethylimidazolium, L" is iodide, and Ar is 3,4-bis(4-methoxyphenyl)-2,5-diphenylcyclopenta-2,4-dienone.

In fact, in a most advantageous manner, when it comprises a step of contacting this primary aliphatic alcohol, preferably ethanol, with a catalyst mixture comprising ruthenium complexes having the above formula II in combination with a base and with an additive of the aforementioned type, the process according to the present invention makes the transformation reaction from primary aliphatic alcohol to a higher alcohol even more efficient towards the formation of the linear dimer in the case of ethanol, or branched higher aliphatic alcohols as main product and of valuable higher alcohols, in mixture or separated, in terms of reaction rate and for the possibility of recycling the catalyst without undergoing an inflection in conversion and yield with respect to the use of other complexes used for this purpose with reference to the background art.

In particular, the use of structurally definable ruthenium ion complexes such as an ionic pair between an anionic ruthenium precursor containing a non-innocent ligand, for example cyclopentadienone or a substituted derivative thereof, and an imidazolium salt improves, if associated with one of the aforementioned additives, the reaction rate, thereby leading to yields and conversions comparable to or better than those of the background art. At the same time, the stability of the aforesaid complex can allow the recovery thereof from the reaction environment, together with the additive, once the products have been separated by distillation, so as to allow the re-use of the complex and of the additive, as will be seen later in relation to a preferred embodiment of the process according to the present invention.

Preferably, in the aforementioned step of the condensation process of a primary aliphatic alcohol, this catalyst is in an amount lower than or equal to 1% by moles on the total moles of this primary aliphatic alcohol, preferably in an amount between 0.005% and 0.5% by moles on the total moles of primary aliphatic alcohol, more preferably in an amount equal to 0.2% by moles on the total moles of such primary aliphatic alcohol.

In an equally preferred manner, in the aforementioned step of the condensation process of a primary aliphatic alcohol, such additive is in an amount between 0.5% and 5% by moles on the total moles of such primary aliphatic alcohol, preferably in an amount equal to 1.5% by moles on the total moles of this primary aliphatic alcohol.

Preferably, in the aforementioned step of the condensation process of a primary aliphatic alcohol, the base is selected from the group consisting of an alkali or alkaline earth metals hydroxide, an alkali or alkaline earth metals alkoxide and any combination thereof. Even more preferably, the base is sodium hydroxide, sodium methoxide, or sodium ethoxide.

In an equally preferred manner, such base is in an amount between 2% and 50% by moles on the total moles of the aforementioned primary aliphatic alcohol, more preferably in an amount equal to 20% by moles on the total moles of such primary aliphatic alcohol.

Preferably, the aforementioned step of the condensation process of a primary aliphatic alcohol is carried out at a temperature from 80 to 170° C., more preferably from 120 to 160° C., still more preferably equal to 150° C.

In an equally preferred manner, the aforementioned step of the condensation process of a primary aliphatic alcohol is carried out for a time between 5 minutes and 24 hours, more preferably for a time between 1 and 8 hours, still more preferably for a time equal to 4 hours.

According to a preferred embodiment, the process according to the present invention, after the aforementioned step of contacting such primary aliphatic alcohol with a catalyst mixture, may provide for the following additional steps:

recycling the aforementioned catalyst and the aforementioned additive, obtaining a recycled catalyst and a recycled additive;

adding the aforementioned base to such recycled catalyst and such recycled additive, obtaining a recycled catalyst mixture;

contacting the aforementioned primary aliphatic alcohol with such recycled catalyst mixture.

In other words, during the aforementioned step of contacting such primary aliphatic alcohol with a catalyst mixture, i.e. once the maximum conversion rate of the aforementioned primary aliphatic alcohol in higher aliphatic alcohols (e.g. n-butanol starting from ethanol as main product), the condensation reaction (Guerbet's reaction) is quenched, and the products mixture is recovered by distillation.

Subsequently, by recycling the catalyst already used for a first condensation cycle and at the same time recycling the additive used for the same first condensation cycle, a suitable amount of base is freshly added to such recycled catalyst and such recycled additive, so as to obtain a recycled catalyst mixture.

Finally, a suitable amount of primary aliphatic alcohol is freshly added to this latter mixture so as to carry out a second condensation cycle and convert this primary aliphatic alcohol into the aliphatic dimer thereof, as main product (n-butanol, when such alcohol primary aliphatic is ethanol), as well as in higher aliphatic alcohols.

Advantageously, this last embodiment of the process according to the present invention allows to recover such catalyst and such additive and to carry out the aforementioned step of contacting the aforementioned primary aliphatic alcohol with a catalyst mixture, in this case a recycled catalyst mixture, allowing to maintain a conversion and yields comparable to the use of the catalyst on first use.

Ultimately, as will be better illustrated below with reference to the Examples in the detailed description, this last embodiment is particularly advantageous and promising in the context of a reactants and starting materials saving, guaranteeing both economic and environmental advantages.

Further characteristics and advantages of the present invention will become apparent from the following description of its preferred embodiments, given by way of non-limiting example.

DETAILED DESCRIPTION

The present invention therefore relates to a condensation process in a homogeneous phase of a primary aliphatic alcohol comprising the step of contacting such primary aliphatic alcohol with a catalyst mixture, wherein such catalyst mixture comprises:

a) a catalyst comprising a complex of a transition metal of groups 7-11, wherein said transition metal is selected from the group consisting of Mn, Re, Fe, Ru, Os, Co, Rh, Ir, Ni, Pd, Pt and Cu;

b) a base;

c) an additive, wherein said additive is selected from any one of the classes of compounds of the group consisting of, isoquinolines N-oxide, quinolines N-oxide, pyridines N-oxide, benzoquinones, naphthoquinones, TEMPO and derivatives thereof.

As anticipated in the summary, the catalyst comprising a complex of a transition metal of groups 7-11, which in its turn comprises a ligand selected from any one of the classes of ligands of the group consisting of imidazolium salts, cyclopentadienones, cyclopentadienyls, carbonyl ligands, anionic ligands, ligands comprising at least one donor nitrogen, phosphine ligands, water, cyclooctadiene, aryls, and a combination thereof.

More particularly, the catalyst comprising a complex of a transition metal of groups 7-11 can comprise, in a completely preferred way, any one of the complexes used in the same class of reactions (Guerbet's reaction) indicated in the following prior art patent documents: WO201531561, US20130116481, U.S. Pat. No. 9,266,807, JP2011136970, JP2011225454; US20100298613, JP2008266267, JP2008303160, and JP2007223947.

In fact, first of all, the process according to the present invention allows to convert a primary aliphatic alcohol into a higher aliphatic alcohol by adding an additive of the aforementioned type to any one of the catalyst mixtures disclosed in the prior art shown in the previous paragraph and comprising a transition metal and a base-based complex. This conversion allows a high yield towards the linear dimer of such primary aliphatic alcohol (when ethanol is used as starting material) and other valuable higher alcohols showing a high flexibility in terms of application to different complexes of transition metals of the aforementioned additives.

Moreover, as anticipated in the summary with reference to the prior art cited in the paragraph relating to the background art, the present invention allows the conversion of a primary aliphatic alcohol into higher aliphatic alcohols (n-butanol as main product, starting from ethanol) with a rate much higher than the one of known transformations carried out in the sole presence of a catalyst comprising a complex of a transition metal of groups 7-11 and of a base, carrying out this transformation in the presence of the same catalyst comprising a complex of a transition metal of groups 7-11 and of the same base, but with the addition of an additive of the aforesaid type.

The present invention will be illustrated below with reference to some examples given by way of non-limiting example.

Example 1: Synthesis of a Ruthenium Complex

With reference to the following Scheme 2, 0.037 g of 1,3-dimethylimidazolium iodide (compound 1a in Scheme 2, 0.166 mmol) were reacted with 0.100 g (0.083 mmol) of dicarbonyl($\eta^4$-3,4-bis(4-methoxyphenyl)-2,5-diphenylcyclopenta-2,4-dienone) ruthenium dimer (compound 2 in Scheme 2) in a solution of $CH_2Cl_2$.

The reaction mixture was left under stirring at room temperature for 30 minutes.

By precipitation with a dichloromethane/n-hexane mixture, a yellow solid was obtained, identified as [dicarbonyl($\eta^4$-3,4-bis (4-methoxyphenyl)-2,5-diphenylcyclopenta-2,4-dienone)(iodine)ruthenium][1,3-dimethylimidazolium] (Complex 3a in Scheme 2).

Complex 3a is stable to air, humidity and dissolved in a solution of non-anhydrous organic solvents.

Scheme 2

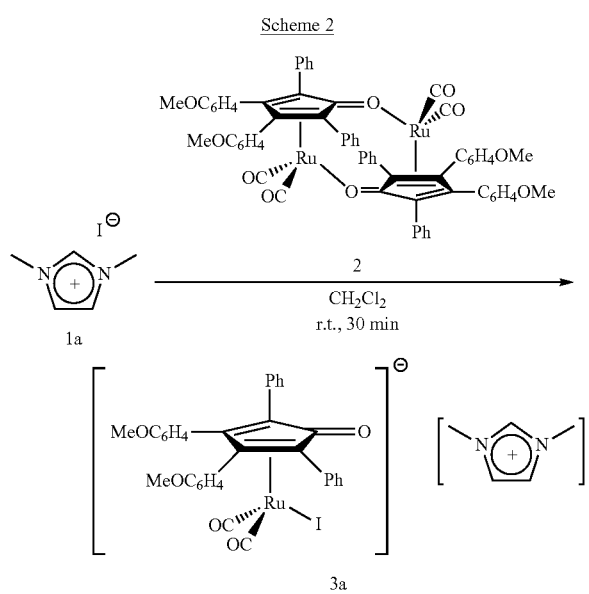

Analysis by infrared spectroscopy, proton NMR analysis ($^1$H-NMR), carbon NMR analysis ($^{13}$C-NMR), mass spectroscopy analysis (ESI-MS), and elemental analysis confirmed the formation of the Complex 3a. The results of the aforementioned analyzes are shown below.

$^1$H-NMR (599.7 MHz, CDCl$_3$): δ 9.91 (s, NCHN), 7.58-6.55 (m, 18H, CH$_{aryl}$), 7.07 (s, 2H, CH$_{im}$), 3.75 (s, 6H, NCH$_3$), 3.70 (s, 6H, —OCH$_3$).

$^{13}$C-NMR (150.8 MHz, CDCl$_3$, g-HSQC, g-HMBC, DEPT): δ 201.00 (CO), 172.12 (C=O, Cp), 158.40 (—COCH$_3$), 138.96 (NCHN), 135.21-112.66 (C$_{aryl}$), 122.55 (CH$_{im}$), 100.09 (C$_{2,5}$, Cp), 81.40 (C$_{3,4}$, Cp), 55.01 (—OCH$_3$), 36.55 (NCH3).

IR (CH$_2$Cl$_2$, cm$^{-1}$): 2004, 1944 ($v_{CO}$); 1580 ($v_{C=O}$), 1604, 1518 ($v_{C=C}$).

ESI-MS (m/z) (+): 97 [M]+; (−): 729 [M]−.

Analysis calculated in percentage (%) for C$_{38}$H$_{33}$IN$_2$O$_5$Ru: C, 55.28; H, 4.03; N, 3.39.

Found: C, 55.26; H, 4.00; N, 3.41.

Example 2: General Procedure for the Conversion of Ethanol to n-Butanol and Higher Alcohols With reference to Scheme 3 below, a 6 mL Schlenk was loaded with 14 mg of the ruthenium complex (Complex 3a in Scheme 2, 0.0172 mmol) synthesized in the previous example (Example 1), with a suitable amount of sodium ethoxide (NaOEt, 122 mg, 1.72 mmol) and with a suitable amount of additive (2,6-dimethoxybenzoquinone, 22 mg, 0.129 mmol).

Subsequently, 0.5 mL of ethanol (8.6 mmol) were added under inert atmosphere to the reaction mixture (the amount of Ru complex on the reagent is 0.2% molar).

Then, the resulting suspension was heated at 150° C. for 4 hours.

At the end of the reaction, the mixture was cooled to room temperature and then stored for 10 minutes in the refrigerator (temperature 4° C.).

Scheme 3

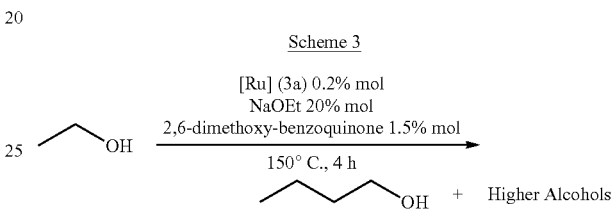

Finally, the mixture was diluted with 3 mL of Et$_2$O and 162 μL of THF were added as an internal standard. The resulting mixture was analyzed by gas chromatography and gas chromatography interfaced with mass spectrometry.

Table 1 below shows the molar amounts of the base and of the additive with respect to the alcohol, as well as the reaction temperature and the reaction time, the ethanol conversion rate, the n-butanol yield, the total yield in alcohols, and the calculated carbon loss (loss).

TABLE 1

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 20 | A | 1.5 | 150 | 4 | 72.1 | 37.5 | 61.0 | 11.1 |

A = 2,6-dimethoxybenzoquinone

Table 1 shows a high conversion and an equally high yield in n-butanol. The selectivity of the reaction with respect to the formation of n-butanol was calculated as follows.

$$\text{Selectivity} = \frac{\text{yield}}{\text{conversion}} * 100$$

wherein $$\text{Yield} = (n_{molCx} * x/2)/n_{molEtOHin}$$

wherein $n_{molCx}$ corresponds to the number of moles of a given obtained higher aliphatic alcohol Cx for which the yield has to be calculated, e.g. n-butanol; wherein x corresponds to the number of carbon atoms of such higher aliphatic alcohol; and, wherein $n_{molEtOHin}$ corresponds to the number of moles of ethanol added to the reaction mixture.

In this case, $$\text{BuOH yield} = (n_{molBuOH(C4)} * 4/2)/n_{molEtOHin}$$

Thus, in the present example a selectivity equal to 51.6% is obtained, which is a better result than the selectivity calculated by the same formula for the same reaction from the data obtained from the document (D. Milstein et al. J. Am. Chem. Soc. 2016, 138, 9077-9080), with reference to the prior art, equal to 48.5%.

Example 3

The procedure reported in the Example 2 above was repeated varying the type of the used base.

The following Table 2 shows the molar amounts of the base, and of the additive with respect to the alcohol, as well as the reaction temperature and the reaction time, the ethanol conversion rate, the n-butanol yield, the total yield in alcohols, and the calculated carbon loss (loss); at first row, the results of Example 2 are given by way of comparison, at second and third rows, the results obtained using sodium hydroxide and sodium methoxide are respectively given.

TABLE 2

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 20 | A | 1.5 | 150 | 4 | 72.1 | 37.5 | 61.0 | 11.1 |
| NaOH | 20 | A | 1.5 | 150 | 4 | 82.8 | 32.8 | 59.6 | 23.1 |
| NaOMe | 20 | A | 1.5 | 150 | 4 | 79.6 | 27.2 | 58.3 | 21.2 |

A = 2,6-dimethoxybenzoquinone

The results show that sodium hydroxide and sodium methoxide are also good candidates as bases to be used in the process of the invention, with particular attention to sodium hydroxide.

In particular, higher conversion values are observed with corresponding lower loss values. The overall alcohols yield remains constant.

Example 4

The procedure reported in Example 2 above was repeated varying the amount of additive used; in addition, p-benzoquinone as an additive was used instead of 2,6-dimethoxybenzoquinone.

The following Table 3 shows the molar amounts of the base and of the additive with respect to the alcohol, as well as the reaction temperature and the reaction time, the ethanol conversion rate, the n-butanol yield, the total yield in alcohols, and the calculated carbon loss (loss).

TABLE 3

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 20 | B | 0.5 | 150 | 4 | 72.4 | 39.0 | 61.9 | 10.4 |
| NaOEt | 20 | B | 1.5 | 150 | 4 | 79.0 | 39.3 | 62.7 | 9.4 |
| NaOEt | 20 | B | 5 | 150 | 4 | 64.4 | 39.3 | 59.4 | 5.1 |

B = p-benzoquinone

As can be seen from Table 3, p-benzoquinone is also a good candidate for use as an additive according to the process of the present invention. Compared to Example 2, the use of p-benzoquinone allows to obtain comparable or even better results. Furthermore, at row 1 it is shown how this type of additive is particularly effective even at relatively low amounts by moles compared to the moles of ethanol (0.5% moles of additive with conversion at 72.4% and selectivity towards n-butanol of 54%).

Also in this case, the selectivity towards n-butanol calculated with the aforesaid method reaches values higher than those of the background art.

Example 5

The procedure reported in Example 2 above was repeated varying the used base amount.

The following table shows the molar amounts of the base and of the additive with respect to the alcohol, as well as the reaction temperature and the reaction time, the ethanol conversion rate, the n-butanol yield, the total yield in alcohols, and the calculated carbon loss (loss); at third row, the results of Example 2 are reported for comparison, at first and second rows the results obtained using lower amounts of base.

TABLE 4

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 0.5 | A | 1.5 | 150 | 4 | 14.5 | 0.6 | 3.1 | 11.4 |
| NaOEt | 10 | A | 1.5 | 150 | 4 | 61.2 | 33.3 | 51.1 | 10.1 |
| NaOEt | 20 | A | 1.5 | 150 | 4 | 72.1 | 37.5 | 61.0 | 11.1 |

A = 2,6-dimethoxybenzoquinone

From Table 4 it can be deduced that even using half base amount, satisfactory ethanol conversion values and corresponding n-butanol yields can be obtained.

Example 6

The procedure reported in Example 2 above was repeated varying the type of used additive.

Depending on the type of additive, appropriate amounts of the same additive and base were used. The reaction temperature and the reaction time were kept equal to those of all previous examples.

Table 5 below shows the molar amounts of the base and of the additive with respect to the alcohol, as well as the reaction temperature and the reaction time, the ethanol conversion rate, the n-butanol yield, the total yield in alcohols, and the calculated carbon loss (loss); at first row, the results of Example 2 are reported for comparison, at second row the results reported at second row of Table 3 (Example 4) are reported for comparison, at third row the results obtained using TEMPO and the results obtained at the fourth row using isoquinoline N-oxide.

TABLE 5

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 20 | A | 1.5 | 150 | 4 | 72.1 | 37.5 | 61.0 | 11.1 |
| NaOEt | 20 | B | 1.5 | 150 | 4 | 79.0 | 39.3 | 62.7 | 9.4 |
| NaOEt | 10 | C | 5 | 150 | 4 | 54.4 | 27.9 | 36.6 | 7.6 |
| NaOEt | 20 | D | 5 | 150 | 4 | 62.5 | 32.2 | 49.3 | 13.2 |

A = 2,6-dimethoxybenzoquinone
B = p-benzoquinone
C = TEMPO

TABLE 5-continued

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|

D = isoquinoline N-oxide

The results show that TEMPO and isoquinoline N-oxide are good candidates, and so are the derivatives thereof, to be used in the process of the invention as additives.

Advantageously, the data shown at row 4 can be obtained with a reaction time of 20 minutes with comparable conversion values and yields.

Example 7

The procedure reported in Example 2 above was repeated. Then, the catalyst, i.e. the Ru complex, was recovered and so was the additive.

In particular, at the end of the condensation reaction of the primary aliphatic alcohol, the obtained products, i.e. n-butanol as main product, valuable higher alcohols and unreacted ethanol, were separated by vacuum distillation.

In this way the catalyst and the additive form a recovery mixture, comprising a recovery catalyst and a recovery additive, which can be re-used for a new condensation cycle after adding a freshly amount of base and a freshly added amount of ethanol.

A suitable amount of sodium ethoxide (NaOEt, 122 mg, 1.72 mmol) was then added to the recovered catalyst and recovered additive.

Subsequently, 0.5 mL of ethanol (8.6 mmol) were added under inert atmosphere to the reaction mixture (the amount of Ru complex with respect to the reagent is equal to 0.2% molar also during the recovery cycle).

Then, the resulting suspension was heated at 150° C. for 4 hours, performing a second recovery cycle for the transformation from ethanol to n-butanol with a catalyst.

At the end of the reaction, the mixture was cooled to room temperature and then stored for 10 minutes in the refrigerator (temperature 4° C.).

Table 6 below shows the molar amounts of the base and of the additive with respect to the alcohol, as well as the reaction temperature and the reaction time, the ethanol conversion rate, the n-butanol yield, the total yield in alcohols, and the calculated carbon loss (loss), obtained both for the first cycle (first row) and for the second recovery cycle (second row).

TABLE 6

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 20 | A | 1.5 | 150 | 4 | 72.1 | 37.5 | 61 | 11.1 |
| NaOEt | 20 | A | 1.5 | 150 | 4 | 67.7 | 35.3 | 52.9 | 14.7 |

A = 2,6-dimethoxybenzoquinone

As can be seen from Table 6, in an extremely advantageous manner, the recycled catalyst (with the additive) keeps the same activity (for the only addition of the fresh base) as can be seen from the comparison with the data of Example 2 reported in row 1.

Example 8—Comparative Example

For comparative purposes, in accordance with a process not according to the invention, a transformation of ethanol into n-butanol and higher alcohols was carried out in the presence of the same Ru complex used in the procedure reported in Example 2 and following.

In particular, a 6 mL Schlenk was loaded with 14 mg of the ruthenium complex (Complex 3a in Scheme 2, 0.0172 mmol) synthesized as in Example 1, with an appropriate amount of sodium ethoxide (NaOEt, 122 mg, 1.72 mmol).

Subsequently, 0.5 mL of ethanol (8.6 mmol) were added under inert atmosphere to the reaction mixture (the amount of Ru complex on the ethanol used as reagent is 0.2% molar).

Then, the resulting suspension was heated at 150° C. for 4 hours.

At the end of the reaction, the mixture was cooled to room temperature and then stored for 10 minutes in the refrigerator (temperature of 4° C.).

Subsequently, the mixture was diluted with 3 mL of Et$_2$O and 162 µL of THF were added as an internal standard. The resulting mixture was analyzed by gas chromatography and gas chromatography on mass spectrometry.

Finally, the procedure was reproduced using a half base amount (NaOEt, 61 mg, 0.86 mmol).

Table 7 below shows the molar amounts of the base and of the additive with respect to the alcohol, as well as the reaction temperature and the reaction time, the ethanol conversion rate, the n-butanol yield, the total yield in alcohols, and the calculated carbon loss (loss).

TABLE 7

| Base | Base (%) | Add. | Add. (%) | T (° C.) | t (h) | EtOH Conv. (%) | BuOH yield (%) | Alcohols yield (%) | Loss (%) |
|---|---|---|---|---|---|---|---|---|---|
| NaOEt | 20 | — | — | 150 | 4 | 45.6 | 31.6 | 42.2 | 3.2 |
| NaOEt | 10 | — | — | 150 | 4 | 31.9 | 19.2 | 23.8 | 8.1 |

As evident from the aforementioned Table 7, both the ethanol conversion values and the n-butanol yield values are significantly lower than the ethanol conversion values and those of the n-butanol yield obtained by performing a procedure using an additive, but with the same type of catalyst, type and base amount, as well as equal reaction conditions, as reported in the Examples 2-5 above.

Example 9: General Procedure for the Conversion of Butanol to Higher Alcohols

With reference to Scheme 4 below, a 6 mL Schlenk was loaded with 8.9 mg of the ruthenium complex (Complex 3a in Scheme 4, 0.0108 mmol) synthesized in the previous Example 1, with a suitable amount of sodium ethoxide (NaOEt, 76 mg, 1.08 mmol) and with a suitable amount of additive (p-benzoquinone, 8.7 mg, 0.081 mmol).

Subsequently, 0.5 mL of butanol (5.4 mmol) were added under inert atmosphere to the reaction mixture (the amount of Ru complex on the reagent was 0.2% molar).

Then, the resulting suspension was heated at 150° C. for 4 hours.

At the end of the reaction, the mixture was cooled to room temperature and then stored for 10 minutes in the refrigerator (temperature: 4° C.).

Scheme 4

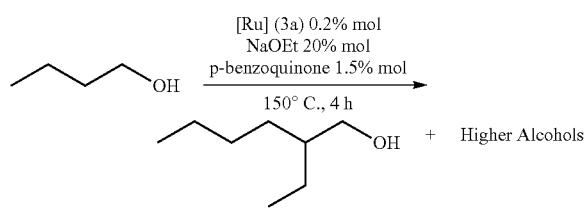

Finally, the mixture was diluted with 3 mL of Et₂O and 162 µL of THF were added as an internal standard. The resulting mixture was analyzed by gas chromatography and gas chromatography interfaced with mass spectrometry.

Table 8 below shows the molar amounts of the base and of the additive with respect to the alcohol, as well as the reaction temperature and the reaction time, the butanol conversion rate, the 2-ethylhexanol yield, the total yield in alcohols, and the calculated carbon loss (loss).

TABLE 8

| Base | Base (%) | Add. | Add. (%) | T (° C.) | t (h) | BuOH Conv. (%) | 2-ethyl-hexanol yield (%) | Alcohols yield (%) | Loss (%) |
|---|---|---|---|---|---|---|---|---|---|
| NaOEt | 20 | B | 1.5 | 150 | 4 | 51.9 | 26.4 | 44.1 | 7.8 |

B = p-benzoquinone

Table 8 shows a satisfactory conversion and an equally satisfactory yield in 2-ethylhexanol.

Example 10

The procedure reported in the Example 9 above was repeated varying the type of the used base.

The following Table 9 shows the molar amounts of the base, and of the additive with respect to the alcohol, as well as the reaction temperature and the reaction time, the butanol conversion rate, the 2-ethylhexanol yield, the total yield in alcohols, and the calculated carbon loss (loss); at first row, the results of Example 9 are given by way of comparison, at second row, the results obtained using sodium hydroxide are given.

TABLE 9

| Base | Base (%) | Add. | Add. (%) | T (° C.) | t (h) | BuOH Conv. (%) | 2-ethyl-hexanol yield (%) | Alcohols yield (%) | Loss (%) |
|---|---|---|---|---|---|---|---|---|---|
| NaOEt | 20 | A | 1.5 | 150 | 4 | 51.9 | 26.4 | 44.1 | 7.8 |
| NaOH | 20 | A | 1.5 | 150 | 4 | 50.5 | 32.9 | 33.8 | 16.7 |

B = p-benzoquinone

Table 9 shows that sodium hydroxide is an effective base in the process according to the present invention when butanol is used as a reagent.

Example 11: General Procedure for the Conversion of 1-Hexanol to Higher Alcohols With reference to Scheme 5 below, a 6 mL Schlenk was loaded with 6.4 mg of the ruthenium complex (Complex 3a in Scheme 5, 0.0078 mmol) synthesized in the previous Example 1, with a suitable amount of sodium ethoxide (NaOEt, 55 mg, 0.78 mmol) and with a suitable amount of additive (p-benzoquinone, 6.3 mg, 0.058 mmol).

Subsequently, 0.5 mL of hexanol (3.9 mmol) were added under inert atmosphere to the reaction mixture (the amount of Ru complex on the reagent was 0.2% molar).

Then, the resulting suspension was heated at 150° C. for 4 hours.

At the end of the reaction, the mixture was cooled to room temperature and then stored for 10 minutes in the refrigerator (temperature: 4° C.).

Scheme 5

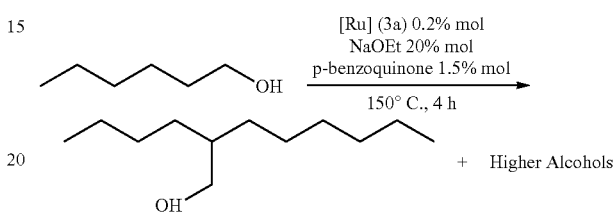

Finally, the mixture was diluted with 3 mL of Et₂O and 162 µL of THF were added as an internal standard. The resulting mixture was analyzed by gas chromatography and gas chromatography interfaced with mass spectrometry.

Table 10 below shows the molar amounts of the base and of the additive with respect to the alcohol, as well as the reaction temperature and the reaction time, the 1-hexanol conversion rate, the 2-butyl-1-octanol yield, the total yield in alcohols, and the calculated carbon loss (loss).

TABLE 10

| Base | Base (%) | Add. | Add. (%) | T (° C.) | t (h) | Hexanol Conv. (%) | 2-butyl-1-octanol yield (%) | Alcohols yield (%) | Loss (%) |
|---|---|---|---|---|---|---|---|---|---|
| NaOEt | 20 | B | 1.5 | 150 | 4 | 61.7 | 29.5 | 45.8 | 15.9 |

B = p-benzoquinone

Table 10 shows a satisfactory conversion and an equally satisfactory yield in 2-butyl-1-octanol.

Example 12

The procedure reported in the Example 11 above was repeated varying the type of the used base.

The following Table 11 shows the molar amounts of the base, and of the additive with respect to the alcohol, as well as the reaction temperature and the reaction time, the hexanol conversion rate, the 2-butyl-1-octanol yield, the total yield in alcohols, and the calculated carbon loss (loss); at first row, the results of Example 11 are given by way of comparison, at second row, the results obtained using sodium hydroxide are given.

TABLE 11

| Base | Base (%) | Add. | Add. (%) | T (° C.) | t (h) | Hexanol Conv. (%) | 2-butyl-1-octanol yield (%) | Alcohols yield (%) | Loss (%) |
|---|---|---|---|---|---|---|---|---|---|
| NaOEt | 20 | A | 1.5 | 150 | 4 | 61.7 | 29.5 | 45.8 | 15.9 |

TABLE 11-continued

| Base | Base (%) | Add. | Add. (%) | T (° C.) | t (h) | Hexanol Conv. (%) | 2-butyl-1-octanol yield (%) | Alcohols yield (%) | Loss (%) |
|---|---|---|---|---|---|---|---|---|---|
| NaOH | 20 | A | 1.5 | 150 | 4 | 56.1 | 30.6 | 31.2 | 24.9 |

B = p-benzoquinone

Table 11 shows that sodium hydroxide is an effective base in the process according to the present invention when 1-hexanol is used as a reagent.

The invention claimed is:

1. A process for the condensation of a primary aliphatic alcohol in a homogeneous phase comprising contacting said primary aliphatic alcohol with a catalyst mixture, wherein said catalyst mixture comprises:
   a) a catalyst comprising a complex of a transition metal of groups 7-11, wherein said transition metal is selected from the group consisting of Mn, Re, Fe, Ru, Os, Co, Rh, Ir, Ni, Pd, Pt and Cu;
   b) a base; and
   c) an additive, wherein said additive is selected from any one of the classes of compounds of the group consisting of pyridines N-oxide, isoquinolines N-oxide, quinolines N-oxide, benzoquinones, naphthoquinones and TEMPO.

2. The process according to claim 1, wherein said additive belongs to the class of pyridines N-oxide and is a substituted pyridine N-oxide, said substituted pyridine N-oxide being substituted in position 2 and/or 3 and/or 4 with one or more substituents individually and independently selected from the group consisting of an aliphatic alkyl group, an aromatic group, halogen, hydroxyl, alkoxyl and a nitro group.

3. The process according to claim 1, wherein said additive is isoquinoline N-oxide, a substituted isoquinoline N-oxide or a substituted quinoline N-oxide, said substituted isoquinoline N-oxide or said substituted quinoline N-oxide being substituted in position 6 and/or 8 with one or more substituents individually and independently selected from the group consisting of an aliphatic alkyl group, an aromatic group, halogen, hydroxyl, alkoxyl and a nitro group.

4. The process according to claim 1, wherein said additive belongs to the class of benzoquinones and is 1,4-benzoquinone or a 2,6-disubstituted p-benzoquinone, said 2,6-disubstituted p-benzoquinone being substituted with substituents individually and independently selected from the group consisting of C2-C4 alkyl, C2-C4 alkoxyl, hydroxyl, amino and —NHCOR, wherein R=C2-C4 alkyl.

5. The process according to claim 1, wherein said additive belongs to the class of naphthoquinones and is a substituted naphthoquinone, said substituted naphthoquinone being substituted in position 2 and/or position 3 with one or more substituents individually and independently selected from the group consisting of an aliphatic alkyl group, hydroxyl, alkoxyl and halogen.

6. The process according to claim 1, wherein said additive belongs to the class of TEMPO and is TEMPO or substituted TEMPO, said substituted TEMPO being substituted in position 4 with a substituent selected from the group consisting of oxo, hydroxyl, alkoxyl, amino group, amide group, carboxyl group and ester group.

7. The process according to claim 1, wherein said primary aliphatic alcohol is a C2-C8 alcohol or any mixture thereof.

8. The process according to claim 1, wherein said catalyst comprising a complex of a transition metal of groups 7-11 comprises a ligand, said ligand being selected from any one of the classes of ligands of the group consisting of imidazolium salts, cyclopentadienones, cyclopentadienyls, carbonyl ligands, anionic ligands, ligands comprising an thereof.

9. The process according to claim 8, wherein said ligand is a ligand comprising an electron donor nitrogen and said ligand being an amine or a pyridine.

10. The process according to claim 8, wherein said ligand is a phosphine and said ligand being an alkyl phosphine or an aryl phosphine.

11. The process according to claim 8, wherein said ligand is an imidazolium salt, said imidazolium salt having the following general Formula I

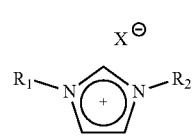

I

R1 and R2 being substituents individually and independently selected from the group consisting of hydrogen, C1-C5 alkyl and aryl; and X being chlorine, bromine or iodine.

12. The process according to claim 11, wherein said imidazolium salt is 1,3-dimethylimidazolyium chloride, 1,3-dimethylimidazolyium bromide or 1,3-dimethylimidazolyium iodide.

13. The process according to claim 8, wherein said catalyst comprising a complex of a transition metal of groups 7-11 is a complex of Formula II

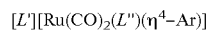

wherein L' is an imidazolium cation or a substituted imidazolium cation, L" being halogen and Ar being aryl.

14. The process according to claim 1, wherein said catalyst is present in an amount lower than or equal to 1% by moles on the total moles of said primary aliphatic alcohol.

15. The process according to claim 1, wherein said additive is present in an amount between 0.5% and 5% by moles on the total moles of said primary aliphatic alcohol.

16. The process according to claim 1, wherein said base is selected from the group consisting of alkali or alkaline earth metal hydroxides, alkali or alkaline earth metal alkoxides and any combination thereof.

17. The process according to claim 1, wherein said base is present in an amount between 2% and 50% by moles on the total moles of said primary aliphatic alcohol.

18. The process according to claim 1, wherein said contacting of said primary aliphatic alcohol with a catalyst mixture is carried out at a temperature between 80° C. and 170° C.

19. The process according to claim 1, wherein said contacting said primary aliphatic alcohol with a catalyst mixture is carried out for a time between 5 minutes and 24 hours.

20. The process according to claim 1 further comprising:
   recycling said catalyst and said additive, obtaining a recycled catalyst and a recycled additive;
   adding said base to said recycled catalyst and said recycled additive, obtaining a recycled catalyst mixture; and contacting said primary aliphatic alcohol with said recycled catalyst mixture.

\* \* \* \* \*